United States Patent [19]

Hoffmann et al.

[11] Patent Number: 5,393,529
[45] Date of Patent: Feb. 28, 1995

[54] ESTROGEN-CONTAINING ACTIVE SUBSTANCE PLASTER

[75] Inventors: Hans-Rainer Hoffmann; Robert P. Klein; Reinhold Meconi, all of Neuwied; Gunter Cordes, Leichingen; Hans M. Wolff, Monheim, all of Germany

[73] Assignees: LTS Lohmann Therapie-Systeme GmbH & Co. KG, Neuwied; Schwarz Pharma AG, Monheim, both of Germany

[21] Appl. No.: 74,698

[22] Filed: Jun. 8, 1993

Related U.S. Application Data

[63] Continuation of Ser. No. 591,171, Oct. 1, 1990, abandoned.

[30] Foreign Application Priority Data

Oct. 6, 1989 [DE] Germany ............... 3933460

[51] Int. Cl.[6] ........................... A61L 15/00
[52] U.S. Cl. ................... 424/445; 424/446; 424/447; 424/448; 424/449
[58] Field of Search ............ 424/444, 445, 446, 447, 424/448, 449; 428/40

[56] References Cited

U.S. PATENT DOCUMENTS

| | | | |
|---|---|---|---|
| 4,039,705 | 8/1977 | Douck et al. | 525/228 |
| 4,687,481 | 8/1987 | Nuwayser | 424/449 |
| 4,810,499 | 3/1989 | Nuwayser | 424/449 |
| 4,818,540 | 4/1989 | Chien et al. | 424/449 |
| 4,906,169 | 3/1990 | Chien et al. | 424/449 |
| 4,913,905 | 4/1990 | Fankhaeuser et al. | 424/449 |

FOREIGN PATENT DOCUMENTS

| | | |
|---|---|---|
| 0072251 | 8/1982 | European Pat. Off. |
| 0186019 | 12/1985 | European Pat. Off. |
| 2094809 | 3/1982 | United Kingdom |
| 8200005 | 6/1981 | WIPO |

OTHER PUBLICATIONS

"National Adhesives" technical bulletin, DUROTAK.

*Primary Examiner*—Thurman K. Page
*Assistant Examiner*—William E. Benston, Jr.
*Attorney, Agent, or Firm*—Sprung Horn Kramer & Woods

[57] ABSTRACT

The present invention relates to active substance plasters for the controlled release of active substances to the skin consisting of a backing layer, an adhesive film connected therewith which film is water-soluble and consists of pressure-sensitive adhesive which comprises water-swellable polymers and in which the active substance is at least partially soluble, and of a removable protective layer covering the adhesive film, in which plasters the pressure-sensitive adhesive is based on homo and/or copolymers with at least one derivative of the acrylic or methacrylic acid, and which comprise as active substances, partially or completely dissolved in the adhesive, at a concentration of 0.5 to 10.0%-wt estrogens and their pharmaceutically acceptable derivatives alone or in combination with gestagens.

8 Claims, No Drawings

ESTROGEN-CONTAINING ACTIVE SUBSTANCE PLASTER

This application is a continuation, of application Ser. No. 07/591,171, filed Oct. 1, 1990 abandoned.

DESCRIPTION

The present invention relates to an active substance containing plaster for the controlled release of active substances to the skin consisting of a backing layer being impermeable to the active substance, a pressure-sensitive adhesive containing the active substance(s), and a removable protective layer, as well as to a process for the production of the active substance containing plaster, and to its use for the transdermal application of estrogens, their pharmaceutically acceptable derivatives alone or in combination with gestagens in human medicine.

Active substance plasters are pressure-sensitive adhesive, galenic preparations to be applied to the skin and which have a fixed application area. They release one or more medicinal agents contained therein to the human or animal body in a controlled manner with respect to time and amount. Such systems, such as are described by Y. W. Chieng, Drug Dev. Ind. Pharm. 13, 589-651 (1987), have proved successful in therapy for years.

Many of these active substance plasters comprise the active substance in a finely divided form within hydrophobic adhesive films, and thus are conceptionally simple pharmaceutical preparations which can be manufactured by series production.

Conventional designs of transdermal systems which are already used in practice are:

a) assembly comprising an impermeable backing layer and a layer simultaneously serving as drug reservoir, pressure-sensitive adhesive, and controlling unit, b) construction of backing layer, drug reservoir, controlling unit, and adhesive layer in spatial separation, c) assembly comprising backing layer and active substance containing matrix being arranged in a multi-layered form, whereby the active substance concentration becomes lower from layer to layer towards the skin, d) construction of backing layer and matrix, whereby the release is controlled by the active substance containing microcapsule being dispersed through the matrix.

Compared to traditional forms of application, the therapeutic progress of these systems lies in the fact that the active substances are not applied to the body in massive doses, such as is the case, for example, when tablets are taken, but in a continuous way.

By this, on the one hand, the duration of effect of the medicinal agent is prolonged, on the other hand, side effects are substantially avoided by the prevention of unnecessary blood level peaks.

If an active substance amount which is higher than the adsorption capacity of the film forming plaster components is incorporated into such a plaster, the active substance is to be distributed within the adhesive matrix as finely as possible up to amorphous, in order to substantially maintain the saturation state of the pressure-sensitive adhesive by rapid subsequent dissolution throughout the duration of application, thus keeping the degree of velocity decrease of the active substance release from the plaster as low as possible. Usually the production of plaster films is carried out in such a way that the adhesive components and the active substance are jointly dissolved in an organic solvent and dried after spreading them on large-surface webs.

It is known from DE-OS 3205258 and EP 0285563 to administer estradiol and ethanol in a plaster formulation at the same time. However, the design of this plaster is very complicated and it can only be produced in a very expensive way, since the individual components must be manufactured separately and are then joined to form a plaster in a further operation.

WO 87/07138 describes an estradiol plaster on the basis of a backing layer, an active substance-containing matrix, and a pressure-sensitive adhesive being covered by a removable protective layer. The production of matrix and pressure-sensitive adhesive is carried out by technologically very expensive operations, such as homogenizing, degasification, coating, drying, and separating. According to one embodiment, the backing layer must even be coated with a pressure-sensitive adhesive thus causing a further operation. Joining together the individual components is carried out in a separate step. Thus, the production of this plaster as a whole is very expensive and complicated.

From U.S. Pat. No. 4,624,665 systems are known which contain the active substance within the reservoir in microencapsulated form. The reservoir is embedded between backing layer and a membrane. The outer edge of the system is provided with a pressure-sensitive adhesive. The construction and the production of these systems is very complicated, since the active substance has to be microencapsulated and homogeneously distributed in a liquid phase which then is embedded between backing layer and membrane by further process steps, In addition, the system is then to be provided with the adhesive edge and covered by a protective layer.

From EP 186019 active substance plasters are known in which water-swellable polymers are added to a rubber/adhesive resin mass, and from which estradiol can be released, However, it turned out that the release of estradiol from these active substance plasters was much to low and did not meet the therapeutic requirements, It is accordingly the object of the present invention to provide an active substance plaster the active substance release of which meets the therapeutic requirements.

Surprisingly, this problem has been solved by the provision of an active substance plaster for the controlled release of active substances to the skin consisting of a backing layer, of a water-insoluble adhesive film connected therewith and made of a pressure-sensitive adhesive which comprises water-swellable polymers and in which the active substances are soluble at least partially, and further consisting of a removable protective layer covering the adhesive film. Said plaster is characterized in that the pressure-sensitive adhesive is based on homopolymers and/or copolymers with at least one derivative of the acrylic or methacrylic acid, and that it comprises as active substances at a concentration of 0.5 to 10.0%-wt partially or completely dissolved in the adhesive estrogens and their pharmaceutically acceptable derivatives alone or in combination with gestagens.

Surprisingly, it turned out that the combination of water-swellable polymers with polymers based on acrylates provided release conditions for the mentioned active substances which, over a longer period of time, guaranteed the release of active substance from the plaster at an amount which was several times over that released according to the state of the art.

A suitable embodiment may comprise substances delaying or preventing the crystallization of the active substance at a concentration of 0.1 to 20%-wt, preferably 0.5 to 10%-wt, as well as water-swellable polymers at a moiety of 0.01 to 10%-wt, preferably 0.1 to 5%-wt. The tackifying resins are advantageously present at an amount of 0.5 to 50%-wt, preferably 1 to 20%-wt. The thickness of the active substance containing adhesive film may amount from 0.01 to 0.30 mm, preferably 0.04 to 0.20 mm.

As pressure-sensitive adhesives homopolymers and/or copolymers with at least one derivative of the acrylic or methacrylic acid in the form of solutions in organic solvents may be used, i.e., in non-cross-linkable or in cross-linkable form. The cross-linking agent has the effect that the polymer chains are linked together via reactive groups and that thus the cohesion of the pressure-sensitive adhesive is increased, The cross-linkable pressure-sensitive adhesives in the form of organic solutions are preferably polymerized from a combination of the following monomers:
2-ethyl hexyl acrylate/n-butyl acrylate/butyl acrylate/acrylic acid,
2-ethyl hexyl acrylate/n-butyl acrylate/vinyl acetate/acrylic acid,
2-ethyl hexyl acrylate/vinyl acetate/acrylic acid,
2-ethyl hexyl acrylate/vinyl acetate/allyl acrylate,
2-ethyl hexyl acrylate/vinyl acetate/divinylbenzene/acrylic acid,
2-ethyl hexyl acrylate/vinyl acetate/allyl methacrylate/acrylic acid,
2-ethyl hexyl acrylate/vinyl acetate/2-hydroxyethyl acrylate,
2-ethyl hexyl 1 acrylate/vinyl acetate/2-hydroxyethyl methacrylate,
2-ethyl hexyl acrylate/fumaric acid-diethyl ester/acrylic acid,
2-ethyl hexyl acrylate/maleic acid-diethyl ester/2hydroxyethyl acrylate.

As cross-linking agents the following compounds are preferred:
diphenylmethane-4-diisocyanate, hexamethylene diisocyanate, isophorone diisocyanate, titanium-acetylacetonate, aluminum-acetylacetonate, iron-acetylacetonate, zinc-acetylacetonate, magnesium-acetylacetonate, zirconium-acetylacetonate, 2-ethyl-l,3-hexanediol-titanate, tetraisooctyl titanate, tetranonyl titanate, polyfunctional propyleneimine derivatives, etherified melamine formaldehyde resins, highly methylated urethane resins, imino-melamine resins.

The non-cross-linkable pressure-sensitive adhesives in the form of organic solutions can advantageously be polymerized, for example, from the combination of the following monomers:
2-ethyl hexyl acrylate/n-butyl acrylate/vinyl acetate,
2-ethyl hexyl acrylate/vinyl acetate,
2-ethyl hexyl acrylate/n-butyl acrylate/vinyl acetate/allyl acrylate,
2-ethyl hexyl acrylate/n-butyl acrylate/allyl methacrylate,
2-ethyl hexyl acrylate/n-butyl acrylate/vinyl acetate/divinylbenzene,
2-ethyl hexyl acrylate/fumaric acid diethyl ester/ allyl acrylate,
2-ethyl hexyl acrylate/maleic acid diethyl ester/allyl acrylate,
2-ethyl hexyl acrylate/n-butyl acrylate/acrylamide/vinyl acetate/allyl acrylate,
2-ethyl hexyl acrylate/n-butyl acrylate/isobutyl acrylate/vinyl acetate/allyl acrylate.

In addition pressure-sensitive adhesives in the form of aqueous dispersions can be used. Their capacity is comparable to that of the solution pressure-sensitive adhesives, however, they have the advantage that in case of coating and drying no inflammable and toxic solvents are formed.

Pressure-sensitive adhesives in the form of aqueous dispersions, so-called dispersion pressure-sensitive adhesives, can, for example, advantageously be polymerized from the combination of the following monomers:
n-butyl acrylate/isobutyl acrylate/acrylic acid,
2-ethyl hexyl acrylate/n-butyl acrylate/acrylic acid,
2-ethyl hexyl acrylate/n-butyl acrylate/2-hydroxyethyl acrylamide,
2-ethyl hexyl acrylate/n-butyl acrylate/vinyl acetate/acrylamide,
2-ethyl hexyl acrylate/n-butyl acrylate/vinyl acetate/2-hydroxyethyl acrylate,
2-ethyl hexyl acrylate/n-butyl acrylate/allyl acrylate/acrylic acid,
2-ethyl hexyl acrylate/n-butyl acrylate/vinyl acetate/divinylbenzene.

In addition, so-called hot-melt pressure-sensitive adhesives can be used, which are applied out of a melt.

Examples of water-swellable polymers added to the adhesive mass of the active substance containing plasters according to the present invention are products, such as galactomannans, cellulose products, tragacanth, polyglycosides, polyvinylpyrrolidones, finely pulverized polyamides, water-soluble polyacrylamide, carboxyvinyl polymers, seaweed products similar to agar, copolymers of methylvinyl ether and maleic acid anhydride, guar gum, types like hydroxypropyl guar gum or guar flour, gum arabic, dextrin and dextran, microbiologically recovered polysaccharide gum, such as the polysaccharide B 1459 or the readily water-soluble type Keltrol and synthetically recovered polysaccharides, such as the product Ficoll, respectively, methylglucose derivatives, hydroxymethylpropyl cellulose, polygalacturonic acid derivatives, such as pectin or the amidated product pectinamide.

In this connection, galactomannans, microcrystalline cellulose and tragacanth are particularly preferred.

In addition tackifying resins, such as colophony and the derivatives therof, polyterpene resins of $\alpha$- or $\beta$-pinene, aliphatic, aromatic, or alkylaromatic hydrocarbon resins, melamine-formaldehyde resins, phenolic resins, hydroabietyl alcohol, and mixtures thereof can be used as components of the pressure-sensitive adhesive.

Further components of the pressure-sensitive adhesive may be crystallization inhibitors, such as phthalic acid esters, adipic acid esters, monoglycerides, diglycerides, and triglycerides, ester of higher fatty acids, long-chain alcohols and the derivatives thereof, derivatives of nonylphenol and octylphenol, respectively, derivatives of fatty acids, derivatives of sorbitol and mannitol, non-ionogenic surfactants, polyoxyethylene alkyl ethers, derivatives of castor oil, sitosterine and polyvinylpyrrolidone, as well as other substances known to those skilled in the art.

The thickness of the active substance containing adhesive film may amount from 0.01 to 0.30 mm, preferably 0.04 to 0.20 mm.

Suitable materials for the backing layer being impermeable to active substances, for example, are polyester, polyamide, polyethylene, polypropylene, polyurethanes, polyvinylchloride, namely both as so-called solo-foils and as sandwich-foils in combination with foils of different plastic materials. These foils may have a thickness of 0.06 to 0.20 mm, and may additionally be aluminized or laminated with an aluminum foil, respectively.

Suitable materials for the removable protective layer, for example, are polyester, polyethylene, and polypropylene, as well as papers coated with these materials and optionally aluminized or laminated with an aluminum foil. In addition, the foils or papers, respectively, are coated with silicone, in order to render them removable. These materials are used at a thickness of 0.02 to 0.30 mm. Except for the polyester foils, these materials can also be used as removable intermediate layers. This is necessary, if the elasticity properties of the removable protective layer and the backing layer are insufficient so that in case of rolling up the laminate of backing layer, active substance containing, water-insoluble adhesive mass, and removable protective layer creases within the active substance plaster would arise after coating and drying.

Suitable active substances according to the present invention are 17 β-estradiol and 17 α-estradiol and the derivatives thereof, respectively.

Pharmaceutically acceptable derivatives according to the present invention are, amongst others, ester, ether, ethynyl compounds of estradiol, such as:

estradiol (17β)-17-butyryl acetate,
estradiol 17 β-cipionate,
estradiol 3,17β-dienantate,
estradiol 3,17β-dipropionate,
estradiolenantate,
estradiol 3-hydrogensulfate (sodium salt),
estradiol 17 β-(3-phenylpropionate),
estradiolundexylate,
estradiolvalerate,
estradiol 17 α-(3-oxohexonate),
epimestrole,
quinestrol,
quinestradol,
ethynylestradiol,
fosferol, and
estratriol, In addition chlorotrianisen is suitable as estrogen, too.

Suitable gestagens according to the present invention, for example, are:

lynestrenol,
norethisterone,
hydroxyprogesterone,
medrogestone,
progesterone,
medroxy progesterone acetate,
gestonorone,
dydrogesterone,
chlormadinone,
allylestrenol,
megestrol.

The process for the production of the active substance plaster is carried out in such a way that all components of the active substance containing adhesive mass are homogenized under stirring or kneading, respectively, optionally with the addition of organic solvents in order to dissolve the active substance. The active substance containing adhesive solution or suspension, respectively, so obtained is coated onto the removable protective layer, the backing layer, or the removable intermediate layer, and the solvent is dried off under increased temperature and/or reduced pressure.

The backing layer, or the removable protective layer, or the removable intermediate layer is laminated on the resulting active substance containing adhesive film.

The broad rolls obtained after coating and drying, consisting of the completely constituted active substance plaster material are cut to narrow rolls, and then the individual active substance plasters are punched. The manufacture of the individual active substance plasters can also be carried out by format punching from the broad rolls.

The active substance containing plasters may have any desired shape, for example, a round, oval, elliptic, square, or rectangular shape with rounded edges. The size of the active substance plasters depends on the therapeutic requirements; it may vary from 1 to 50 $cm^2$.

The invention will be illustrated by the following examples:

EXAMPLE 1

| | |
|---|---|
| 182.342 g | cross-linkable pressure-sensitive adhesive based on homo and/or copolymers with at least one derivative of the acrylic or methacrylic acid with cross-linking agent (e.g., Durotak 280-2516), |
| 1.64 g | galactomannan (e.g., Meyprogat 90), |
| 1.60 g | 1,2-propanediol and |
| 2.00 g | estradiol are homogenized by stirring in a beaker under the addition of |
| 8.773 g | ethanol and |
| 8.773 g | ethyl acetate. |

2.00 g estradiol are homogenized by stirring in a beaker under the addition of 8,773 g ethanol and 8.773 g ethyl acetate.

This mass is spread by means of a coating bar on a polyester foil having a thickness of 100 μm which is aluminized one side and coated with silicone on both sides; the mass is dried at 50° C. in a circulating-air-drying-chamber for 10 minutes so that an active substance containing adhesive film having an area weight of 80 $g/m^2$ results. This film is subsequently covered with a polyester foil of 15 μm thickness. Then individual plasters having a surface of 16 $cm^2$ are punched out.

Active substance release

Plaster sections of 5 $cm^2$ are used for the measurement of the active substance release.

On the side of the backing layer the active substance plaster is agglutinated with a polyester foil of 100 μm thickness and, after having pulled-off the removable protective layer, inserted into 80 ml demineralized water of 34° C. After 2, 4, 6, and 24 hours, the demineralized water is changed and the estradiol content in the sample solutions determined by liquid chromatography.

The results are shown in Table 1.

The further examples differ in the pressure-sensitive adhesive used. The results of the active substance release are summarized in Table 1.

EXAMPLE 2

| | |
|---|---|
| 148.00 g | non-cross-linkable pressure-sensitive adhesive based on homo and/or copolymers with |

| | |
|---|---|
| | at least one derivative of the acrylic or methacrylic acid (e.g., Durotak 280-2287) |
| 2.40 g | galactomannan (e.g., Meyprogat 90), |
| 1.60 g | 1,2-propanediol and |
| 2.00 g | estradiol are homogenized by stirring in a beaker under the addition of |
| 30.667 g | ethanol and |
| 15.337 g | ethyl acetate |

Further processing is carried out as described in Example 1.

EXAMPLE 3

| | |
|---|---|
| 140.26 g | cross-linkable pressure-sensitive adhesive based on homo and/or copolymers with at least one derivative of the acrylic or methacrylic acid with cross-linking agent (e.g., Durotak 126-1050) |
| 1.64 g | galactomannan (e.g., Meyprogat 90), |
| 1.60 g | 1,2-propanediol and |
| 2.00 g | estradiol are homogenized in a beaker by stirring under the addition of |
| 20 ml | ethanol and |
| 20 ml | ethyl acetate |

Further processing is carried out as described in Example 1.

EXAMPLE 4

| | |
|---|---|
| 155.43 g | cross-linkable pressure-sensitive adhesive based on homo and/or copolymers with at least one derivative of the acrylic or methacrylic acid with cross-linking agent (e.g., Durotak 380-1054) |
| 1.64 g | galactomannan (e.g., Meyprogat 90), |
| 1.60 g | 1,2-propanediol and |
| 2.00 g | estradiol are homogenized in a beaker by stirring. |

Further processing is carried out as described in Example 1.

EXAMPLE 5

| | |
|---|---|
| 153.20 g | cross-linkable pressure-sensitive adhesive based on homo and/or copolymers with at least one derivative of the acrylic or methacrylic acid with cross-linking agent (e.g., Durotak 180-1197B) |
| 1.64 g | galactomannan (e.g., Meyprogat 90), |
| 1.60 g | 1,2-propanediol and |
| 2.00 g | estradiol are homogenized by stirring in a beaker under the addition of |
| 20.00 ml | ethanol and |
| 20.00 ml | ethyl acetate |

Further processing is carried out as described in Example 1.

EXAMPLE 6

| | |
|---|---|
| 146.88 g | cross-linkable pressure-sensitive adhesive based on homo and/or copolymers with at least one derivative of the acrylic or methacrylic acid with cross-linking agent (e.g., Aroset 1880-Z-46) |
| 1.64 g | galactomannan (e.g., Meyprogat 90), |
| 1.60 g | 1,2-propanediol and |
| 2.00 g | estradiol are homogenized in a beaker by stirring under the addition of |
| 20.00 ml | ethanol and |
| 20.00 ml | ethyl acetate |

Further processing is carried out as described in Example 1.

EXAMPLE 7

| | |
|---|---|
| 139.22 g | cross-linkable pressure-sensitive adhesive based on homo and/or copolymers with at least one derivative of the acrylic or methacrylic acid with cross-linking agent (e.g., Aroset 1930-TH-46) |
| 1.64 g | galactomannan (e.g., Meyprogat 90), |
| 1.60 g | 1,2-propanediol and |
| 2.00 g | estradiol are homogenized by stirring in a beaker under the addition of |
| 30.00 ml | ethanol and |
| 30.00 ml | ethyl acetate |

Further processing is carried out as described in Example 1.

TABLE 1

Prior art according to EP 0186019 - Example 3 C
Active substance release: 0.63 mg/16 cm$^2$ × 24 hours.

| | Active substance release mg/16 cm$^2$ after | | | | |
|---|---|---|---|---|---|
| Example | 2 h | 4 h | 6 h | 8 h | 24 h |
| 1 | 0.67 | 1.10 | 1.63 | — | 2.38 |
| 2 | 0.77 | 1.24 | 1.85 | — | 2.67 |
| 3 | 0.88 | 1.37 | — | 1.63 | 2.87 |
| 4 | 0.74 | 1.19 | — | 1.77 | 2.43 |
| 5 | 0.62 | 1.01 | — | 1.49 | 2.28 |
| 6 | 0.66 | 1.00 | — | 1.51 | 2.36 |
| 7 | 0.81 | 1.28 | — | 1.91 | 2.71 |

As is demonstrated by the results of Table 1, the active substance release of the plasters according to the present invention—already after 2 hours—is as high as that according to the state of the art is after 24 hours.

It is understood that the specification and examples are illustrative but not limitative of the present invention and that other embodiments within the spirit and scope of the invention will suggest themselves to those skilled in the art.

We claim:

1. In a plaster for the controlled release of an estrogen to the skin and comprising A) an impermeable backing or covering layer, B) a reservoir layer adjacent to, and in close contact with said backing or covering layer, said reservoir layer comprising a water-insoluble pressure-sensitive adhesive polymer layer containing the estrogen in a concentration of about 0.5 to 10 by weight, in combination with at least one water-swellable polymer in 0.01 to 10% wt, and C) a protective layer covering and adhering to said adhesive polymer layer and removable therefrom for the use of said transdemal drug patch, the improvement wherein the pressure-sensitive adhesive polymer of B is a polymer of acrylic or methacrylic acid or an ester thereof, and contains a 0.1 to 20%-wt of at least one substance delaying or preventing the crystallization of the active substance, the water-swellable polymer being selected from the group consisting of galactomannans, cellulose products, tragacanth, polyglycosides, polyvinylpyrrolidones, finely pulverized polyamides, water-soluble polyacrylamide, carboxyvinyl polymers, agar, copolymers of methylvinyl ether and maleic acid anhydride, guar gum, hydroxypropyl guar gum or guar flour, gum arabic, dextrin and dextran, polysaccharide gum, hydroxymethylpropyl cellulose, pectin and pectinamide, and the crystallization delaying or preventing substance being selected from the group consisting of phthalic acid esters, adipic acid esters, monoglycerides, diglycerides, and triglycerides, ester of higher fatty acids, long-chain alcohols, nonylphenol, octylphenol, fatty acids, sorbitol, mannitol, non-ionogenic surfactants, polyoxyethylene alkyl esters, castor oil, sitosterine and polyvinylpyrrolidone.

2. A plaster according to claim 1, wherein the polymer of B is cross-linkable.

3. A plaster according to claim 1, wherein the polymer of B is a solvent-based pressure-sensitive adhesive.

4. A plaster according to claim 1, wherein the polymer of B is a dispersion-based pressure-sensitive adhesive.

5. A plaster according to claim 1, wherein the polymer of C is a hot-melt-pressure-sensitive adhesive.

6. A plaster according to claim 1, wherein the pressure-sensitive adhesive comprises at least one tackifying resin in an amount of 0.5 to 50%-wt.

7. A plaster according to claim 1, wherein the therapeutic substance-containing adhesive film has a thickness of 0.01 to 0.3 mm.

8. A plaster according to claim 1, wherein the additionally water-swellable polymer of layer C is selected from the group consisting of galactomannan, microcrystalline cellulose and tragacanth.

* * * * *

UNITED STATES PATENT AND TRADEMARK OFFICE
CERTIFICATE OF CORRECTION

PATENT NO. : 5,393,529

DATED : February 28, 1995

INVENTOR(S) : Hoffmann, et al.

It is certified that error appears in the above-identified patent and that said Letters Patent is hereby corrected as shown below:

Col. 10, line 7    Delete " C " and substitute -- B --

Col. 10, line 15   Delete " C " and substitute -- B --

Signed and Sealed this

Thirtieth Day of May, 1995

*Attest:*

*Attesting Officer*

BRUCE LEHMAN

*Commissioner of Patents and Trademarks*

(12) EX PARTE REEXAMINATION CERTIFICATE (6849th)
United States Patent
Hoffmann et al.

(10) Number: US 5,393,529 C1
(45) Certificate Issued: Jun. 2, 2009

(54) ESTROGEN-CONTAINING ACTIVE SUBSTANCE PLASTER

(75) Inventors: Hans-Rainer Hoffmann, Neuwied (DE); Robert P. Klein, Neuwied (DE); Reinhold Meconi, Neuwied (DE); Gunter Cordes, Leichingen (DE); Hans M. Wolff, Monheim (DE)

(73) Assignee: LTS Lohmann Therapie-Systeme AG, Andernach (DE)

Reexamination Request:
No. 90/006,899, Dec. 31, 2003

Reexamination Certificate for:
Patent No.: 5,393,529
Issued: Feb. 28, 1995
Appl. No.: 08/074,698
Filed: Jun. 8, 1993

Related U.S. Application Data

(63) Continuation of application No. 07/591,171, filed on Oct. 1, 1990, now abandoned.

(30) Foreign Application Priority Data

Oct. 6, 1989 (DE) .............................. 3933460

(51) Int. Cl.
*A61L 15/00* (2006.01)

(52) U.S. Cl. .................. 424/445; 424/446; 424/447; 424/448; 424/449

(58) Field of Classification Search ............... 424/448, 424/449, 484
See application file for complete search history.

(56) References Cited

U.S. PATENT DOCUMENTS

| | | | |
|---|---|---|---|
| 2,861,920 A | 11/1958 | Jack et al. | 514/39 |
| 3,632,740 A | 1/1972 | Robinson et al. | 424/448 |
| 4,039,705 A | 8/1977 | Douek et al. | 525/228 |
| 4,331,651 A | 5/1982 | Beul et al. | |
| 4,409,200 A | 10/1983 | Feller et al. | 436/516 |
| 4,608,249 A | 8/1986 | Otsuka et al. | 424/448 |
| 4,655,768 A | 4/1987 | Marecki et al. | 424/448 |
| 4,668,232 A | 5/1987 | Cordes et al. | 424/448 |
| 4,687,481 A | 8/1987 | Nuwayser | 424/449 |
| 4,810,499 A | 3/1989 | Nuwayser | 424/449 |
| 4,818,540 A | 4/1989 | Chien et al. | 424/449 |
| 4,906,169 A | 3/1990 | Chien et al. | 424/449 |
| 4,906,475 A * | 3/1990 | Kim | 424/449 |
| 4,913,905 A | 4/1990 | Fankhaeuser et al. | 424/449 |
| 5,252,334 A | 10/1993 | Chiang et al. | 424/445 |

FOREIGN PATENT DOCUMENTS

| | | |
|---|---|---|
| EP | 0 072 251 | 8/1982 |
| EP | 156080 | 10/1985 |
| EP | 0 186 019 | 12/1985 |
| EP | 209975 | 1/1987 |
| EP | 223524 | 5/1987 |
| EP | 272987 | 6/1988 |
| EP | 275716 | 7/1988 |
| EP | 279977 | 8/1988 |
| EP | 328806 | 8/1989 |
| EP | 379045 | 7/1990 |
| EP | 416842 | 3/1991 |
| GB | 2094809 | 3/1982 |
| GB | 2086224 | 5/1982 |
| WO | WO 82/00005 | 6/1981 |
| WO | WO 87/107138 | 12/1987 |
| WO | WO 88/01496 | 3/1988 |
| WO | WO 89/07950 | 9/1989 |
| WO | WO 89/07951 | 9/1989 |

OTHER PUBLICATIONS

D. Satas, "Handbook f Pressure Sensitive Adhesive Technology", 2nd ed., (1982).
Mutschler, Ernst, Textbook of Pharmacology and Toxicology, pp. 2–11, 1986.
Hadgraft, Guy (Eds.) "Transdermal Drug Delivery: developmental issues and research initiatives" Marcel Dekker Inc., New York (1989) pp. 197–245.
Smith Maibach: "Percutaneous permeation enhancers", CRC Press, New York (1985) pp. 277–287.
D. Satas, "Handbook of Pressure Sensitive Adhesive Technology", $2^{nd}$ ed., (1982).

* cited by examiner

*Primary Examiner*—Isis Ghali

(57) ABSTRACT

The present invention relates to active substance plasters for the controlled release of active substances to the skin consisting of a backing layer, an adhesive film connected therewith which film is water-soluble and consists of pressure-sensitive adhesive which comprises water-swellable polymers and in which the active substance is at least partially soluble, and of a removable protective layer covering the adhesive film, in which plasters the pressure-sensitive adhesive is based on homo and/or copolymers with at least one derivative of the acrylic or methacrylic acid, and which comprise as active substances, partially or completely dissolved in the adhesive, at a concentration of 0.5 to 10.0%-wt estrogens and their pharmaceutically acceptable derivatives alone or in combination with gestagens.

US 5,393,529 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2–8 are cancelled.

Claim 1 is determined to be patentable as amended.

New claims 9–12 and 13 are added and determined to be patentable.

1. In a plaster for the controlled release of an estrogen to the skin [and], comprising:
   A) an impermeable backing or covering layer[,] ;
   B) a reservoir layer adjacent to, and in close contact with [said] *the* backing or covering layer, [said] *the* reservoir layer comprising a water-insoluble pressure sensitive adhesive polymer [layer] containing the estrogen in a concentration of about 0.5 to 10% by weight, in combination with at least one water-swellable polymer in 0.01 to 10% [wt.] *by weight;* and
   C) a protective layer covering and adhering to [said] *the* adhesive polymer [layer] and removable therefrom for the use of [said transdermal drug patch,] *the plaster;*
   the improvement wherein the *reservoir layer comprises a water-insoluble* pressure-sensitive adhesive polymer [of B] *which* is a polymer of acrylic or methacrylic acid or an ester thereof, and contains a 0.1 to 20% [-wt] *by weight* of at least one substance delaying or preventing the crystallization of the [active substance] *estrogen*, and
   *wherein* the water-swellable polymer [being selected from the group consisting of galactomannans, cellulose products, tragacanth, polyglycosides, polyvinylpyrrolidones, finely pulverized polyamides, water-soluble polyacrylamide, carboxyvinyl polymers, agar, copolymers of methylvinyl ether and maleic acid anhydride, guar gum, hydroxypropyl guar gum or guar flour, gum arabic, dextrin and dextran, polysaccharide gum, hydroxymethylpropyl cellulose, pectin and pectinamide] *is a galactomannan,* and *further*
   *wherein* the crystallization delaying or preventing substance [being] *is* selected from the group consisting of phthalic acid esters, adipic acid esters, monoglycerides, diglycerides, and triglycerides, ester of higher fatty acids, long-chain alcohols, nonylphenol, octylphenol, fatty acids, sorbitol, mannitol, non-ionogenic surfactants, polyoxyethylene alkyl esters, castor oil, *and* sitosterine [and polyvinylpyrrolidone].

*9. In a plaster for the controlled release of an estrogen to the skin comprising:*
   *A) an impermeable backing or covering layer;*
   *B) a reservoir layer adjacent to, and in close contact with the backing or covering layer; the reservoir layer comprising a water-insoluble pressure sensitive adhesive polymer containing the estrogen in a concentration of about 0.5 to 10% by weight, in combination with at least one water-swellable polymer in 0.01 to 10% by weight; and*
   *C) a protective layer covering and adhering to the adhesive polymer and removable therefrom for the use of the plaster;*
   *the improvement wherein the reservoir layer comprises a water-insoluble pressure-sensitive adhesive polymer which is a polymer of acrylic or methacrylic acid or an ester thereof, and contains a 0.1 to 20% by weight of at least one substance delaying or preventing the crystallization of the estrogen, and*
   *wherein the water-swellable polymer is a galactomannan, and*
   *wherein the crystallization delaying or preventing substance is selected from the group consisting of phthalic acid esters, adipic acid esters, monoglycerides, diglycerides, and triglycerides, ester of higher fatty acids, long-chain alcohols, nonylphenol, octylphenol, fatty acids, sorbitol, mannitol, non-ionogenic surfactants, polyoxyethylene alkyl esters, castor oil, sitosterine, and polyvinylpyrrolidone, and wherein the amount of water-swellable polymer and the amount of crystallization delaying or preventing substance present in the combination is that which enhances the release of estrogen to the skin.*

*10. A plaster for the controlled release of an estrogen to the skin comprising:*
   *an impermeable backing layer;*
   *a reservoir layer, on one face adjacent to and in close contact with the backing layer, comprising a water-insoluble pressure sensitive adhesive polymer containing estrogen at a concentration of 0.5 to 10% by weight, at least one water-swellable polymer at a concentration of 0.01 to 10% by weight; and at least one crystallization delaying or preventing substance at a concentration of 0.1 to 20% by weight; and*
   *a removable protective layer covering and adhering to the opposite face of the reservoir layer;*
   *wherein the pressure-sensitive adhesive polymer of the reservoir layer is a polymer of acrylic or methacrylic acid or an ester thereof, and*
   *wherein the water-swellable polymer is a galactomannan, and*
   *wherein the crystallization delaying or preventing substance is selected from the group consisting of phthalic acid esters, adipic acid esters, monoglycerides, diglycerides, and triglycerides, ester of higher fatty acids, long-chain alcohols, nonylphenol, octylphenol, fatty acids, sorbitol, mannitol, non-ionogenic surfactants, polyoxyethylene alkyl esters, castor oil, sitosterine, and polyvinylpyrrolidone, and wherein the amount of water-swellable polymer and crystallization delaying or preventing substance in the reservoir layer enhances the release of the estrogen to the skin.*

*11. In a plaster for the controlled release of an estrogen to the skin comprising:*
   *A) an impermeable backing or covering layer;*
   *B) a reservoir layer adjacent to, and in close contact with the backing or covering layer, the reservoir layer comprising a water-insoluble pressure sensitive adhesive polymer containing the estrogen in a concentration of about 0.5 to 10% by weight, in combination with at least one water-swellable polymer in 0.01 to 5% by weight; and*
   *C) a protective layer covering and adhering to the adhesive polymer and removable therefrom for the use of the plaster;* the improvement wherein the reservoir layer comprises a water-insoluble pressure-sensitive adhesive polymer which is a polymer of acrylic or methacrylic acid or an ester thereof, and contains a 0.1 to 10% by weight of at least one substance delaying or preventing the crystallization of the estrogen, and wherein the water-swellable polymer is a galactomannan, and wherein the crystallization delaying or preventing substance is selected from the group consisting of phthalic acid esters, adipic acid esters, monoglycerides, diglycerides, and triglycerides, ester of higher fatty acids, long-chain alcohols, nonylphenol, octylphenol, fatty acids, sorbitol, mannitol, non-ionogenic surfactants, polyoxyethylene alkyl esters, castor oil, sitosterine, and polyvinylpyrrolidone.

12. A method of preventing the crystallization of an estrogen in a plaster for the controlled release of the estrogen to the skin by adding a crystallization delaying or preventing substance to the plaster, wherein the plaster comprises:

A) an impermeable backing or covering layer;

B) a reservoir layer adjacent to, and in close contact with the backing or covering layer, the reservoir layer comprising a water-insoluble pressure sensitive adhesive polymer containing the estrogen in a concentration of about 0.5 to 10% by weight, in combination with at least one water-swellable polymer in 0.01 to 10% by weight; and C) a protective layer covering and adhering to the adhesive polymer and removable therefrom for the use of plaster;

the improvement wherein the reservoir layer comprises a water-insoluble pressure-sensitive adhesive polymer which is a polymer of acrylic or methacrylic acid or an ester thereof, and contains a 0.1 to 20% by weight of at least one substance delaying or preventing the crystallization of the estrogen, and wherein the water-swellable polymer is a galactomannan, and wherein the crystallization delaying or preventing substance is selected from the group consisting of phthalic acid esters, adipic acid esters, monoglycerides, diglycerides, and triglycerides, ester of higher fatty acids, long-chain alcohols, nonylphenol, octylphenol, fatty acids, sorbitol, mannitol, non-ionogenic surfactants, polyoxyethylene alkyl esters, castor oil, sitosterine, and polyvinylpyrrolidone, and wherein the amount of water-swellable polymer and the amount of crystallization delaying or preventing substance present in the combination is that which enhances the release of estrogen to the skin.

13. In a plaster for the controlled release of an estrogen to the skin comprising:

A) an impermeable backing or covering layer;

B) a reservoir layer adjacent to, and in close contact with the backing or covering layer, the reservoir layer comprising a water-insoluble pressure sensitive adhesive polymer containing the estrogen in a concentration of about 0.5 to 10% by weight, in combination with at least one water-swellable polymer in 0.01 to 10% by weight; and C) a protective layer covering and adhering to the adhesive polymer and removable therefrom for the use of the plaster;

the improvement wherein the reservoir layer comprises a water-insoluble pressure-sensitive adhesive polymer which is a polymer of acrylic or methacrylic acid or an ester thereof, and contains a 0.1 to 20% by weight of at least one substance delaying or preventing the crystallization of the estrogen, and wherein the water-swellable polymer is a galactomannan, and wherein the crystallization delaying or preventing substance is selected from the group consisting of phthalic acid esters, adipic acid esters, monoglycerides, diglycerides, and triglycerides, ester of higher fatty acids, long-chain alcohols, nonylphenol, octylphenol, fatty acids, sorbitol, mannitol, non-ionogenic surfactants, polyoxyethylene alkyl esters, castor oil, sitosterine, and polyvinylpyrrolidone, and wherein the pressure-sensitive adhesive polymer consists of a cross-linked copolymer obtained from polymerization of 2-ethylhexyl acrylate, vinyl acetate, and 2-hydroxyethyl acrylate monomers.

\* \* \* \* \*